United States Patent
Chang et al.

(10) Patent No.: US 10,925,522 B2
(45) Date of Patent: Feb. 23, 2021

(54) METHOD, SYSTEM, AND COMPUTER PROGRAM PRODUCT FOR DYNAMIC ANALYSIS OF A PHYSIOLOGICAL PARAMETER

(71) Applicant: BIONIME CORPORATION, Taichung (TW)

(72) Inventors: Ming-Luen Chang, Taichung (TW); Cheng-Wei Lu, Taichung (TW)

(73) Assignee: Bionime Corporation, Taichung (TW)

(*) Notice: Subject to any disclaimer, the term of this patent is extended or adjusted under 35 U.S.C. 154(b) by 385 days.

(21) Appl. No.: 15/866,774

(22) Filed: Jan. 10, 2018

(65) Prior Publication Data
US 2018/0199867 A1    Jul. 19, 2018

(30) Foreign Application Priority Data
Jan. 16, 2017 (TW) .................. 10610135.4

(51) Int. Cl.
| | | |
|---|---|---|
| *A61B 5/00* | (2006.01) | |
| *A61B 5/145* | (2006.01) | |
| *G16H 40/67* | (2018.01) | |
| *G16H 50/20* | (2018.01) | |
| *G16H 50/30* | (2018.01) | |

(52) U.S. Cl.
CPC ........ *A61B 5/14532* (2013.01); *A61B 5/0022* (2013.01); *G16H 40/67* (2018.01); *G16H 50/20* (2018.01); *G16H 50/30* (2018.01)

(58) Field of Classification Search
CPC .. A61B 5/14532; A61B 5/0022; G16H 50/30; G16H 50/20; G16H 40/67
See application file for complete search history.

(56) References Cited

U.S. PATENT DOCUMENTS

| | | | |
|---|---|---|---|
| 9,220,456 B2 | 12/2015 | Bashan | |
| 2007/0118054 A1* | 5/2007 | Pinhas | A16B 5/4812 600/587 |

(Continued)

FOREIGN PATENT DOCUMENTS

| | | |
|---|---|---|
| CN | 103561634 A | 2/2014 |
| CN | 103025242 B | 12/2015 |
| KR | 20140082460 A | 7/2014 |

OTHER PUBLICATIONS

Search Report Issued in European Counterpart Application No. 18151715.2 by the EPO dated Jul. 3, 2018.

*Primary Examiner* — Navin Natnithithadha
*Assistant Examiner* — Andrey Shostak
(74) *Attorney, Agent, or Firm* — Rosenberg, Klein & Lee

(57) ABSTRACT

A method for dynamic analysis of a physiological parameter of a user includes: generating a first event label corresponding to a first measurement value of the physiological parameter measured at a first time point; generating a second event label corresponding to a second measurement value of the physiological parameter measured at a second time point; calculating a time difference between the first and second time points; calculating a measurement value difference between the first and second measurement values when a time difference between the first and second time points is smaller than a time length threshold; and providing an analysis outcome based on the first and second event labels and the measurement value difference.

19 Claims, 12 Drawing Sheets

(56) References Cited

U.S. PATENT DOCUMENTS

| | | | | |
|---|---|---|---|---|
| 2011/0148905 A1* | 6/2011 | Simmons | ............ | A63B 71/0619 |
| | | | | 345/589 |
| 2011/0319322 A1* | 12/2011 | Bashan | ............... | G06F 19/3456 |
| | | | | 514/5.9 |
| 2012/0173161 A1* | 7/2012 | Virkamaki | ......... | A61B 5/14532 |
| | | | | 702/21 |
| 2013/0190583 A1* | 7/2013 | Grosman | ........... | A61B 5/14532 |
| | | | | 600/365 |
| 2014/0035558 A1* | 2/2014 | Niwa | ..................... | G01D 18/00 |
| | | | | 324/76.11 |
| 2015/0164383 A1* | 6/2015 | Varsaysky | .......... | A61B 5/14556 |
| | | | | 600/316 |
| 2016/0231308 A1* | 8/2016 | Esser | ..................... | G01N 33/49 |
| 2017/0220751 A1* | 8/2017 | Davis | ................... | A61B 5/0015 |

\* cited by examiner (a)

(b)

(c)

(d)

| 2015 Aug. | Breakfast | | Lunch | | Dinner | | Bedtime |
|---|---|---|---|---|---|---|---|
| 09 Mon (12) | 245\| | | 114\| | | 183\| | | 138 |
| 08 Sat (12) | 242\| | | 157\|183 | | \| | | 219 |
| 07 Fri (12) | 218\| | | 108\|330 | | 127\| | | 218 |
| 06 Thu (12) | | | 139\|195 | | \| | | 207 |
| 05 Wed (12) | 241\| | | 120\| | | 100\|190 | | |
| 04 Tue (12) | 197\| | | 114\| | | 147\|255 | | |

| 2016 November | Breakfast | Lunch | Dinner |
|---|---|---|---|
| 15 Tue | — | 98\|113 | — |
| 14 Mon | 95\|116 | — | 96 |
| 13 Sun | — | — | — |
| 12 Sat | — | — | — |
| 11 Fri | — | — | — |
| 10 Thu | 106 | — | 90\|151\|132 |

FIG.6

METHOD, SYSTEM, AND COMPUTER PROGRAM PRODUCT FOR DYNAMIC ANALYSIS OF A PHYSIOLOGICAL PARAMETER

CROSS-REFERENCE TO RELATED APPLICATION

This application claims priority of Taiwanese Patent Application No. 106101354, filed on Jan. 16, 2017.

FIELD

The disclosure relates to a method, a system and a computer program product for dynamic analysis of a physiological parameter.

BACKGROUND

A conventional computer program for blood glucose analysis requires pre-setting of breakfast time, lunch time and dinner time so as to remind the user to measure his/her blood glucose level before and after meal. However, the dining time may vary among weekdays and holidays or due to schedule changes, so the pre-setting of dining time is not a convenient design. In addition, neglecting the effects of food consumption other than the regular meals may lead to imprecision in the analysis of blood glucose variation, and in turn adversely affect the treatment for diabetes, which is to be decided by a doctor.

SUMMARY

Therefore, an object of the disclosure is to provide a method, a system and a computer program for dynamic analysis of a physiological parameter of the user that can alleviate at least one of the drawbacks of the prior art.

According to the disclosure, the method is to be implemented by a computerized physiological parameter analysis system, and includes: generating a first event label corresponding to a first measurement value of the physiological parameter of the user measured at a first time point; generating a second event label corresponding to a second measurement value of the physiological parameter of the user measured at a second time point; calculating a time difference between the first and second time points; determining whether or not the time difference is smaller than a first time length threshold; upon determining that the time difference is smaller than the first time length threshold, calculating a measurement value difference between the first and second measurement values; and providing an analysis outcome based on the first event label, the second event label, and the measurement value difference.

According to the disclosure, the system for analysis of a physiological parameter of a user includes a measurement part configured to measure the physiological parameter of the user for generating a first event label corresponding to a first measurement value of the physiological parameter of the user measured at a first time point and a second event label corresponding to a second measurement value of the physiological parameter of the user measured at a second time point; and a computation part communicatively coupled to the measurement part for receiving therefrom measured physiological parameter data including the first event label, the first measurement value, the first time point, the second event label, the second measurement value and the second time point, and configured: to calculate a time difference between the first and second time points; to determine whether or not the time difference is smaller than a first time length threshold; to calculate, upon determining that the time difference is smaller than the first time length threshold, a measurement value difference between the first and second measurement values; and to provide an analysis outcome based on the first event label, the second event label, and the measurement value difference.

According to the disclosure, the computer program for analysis of a physiological parameter of a user includes instructions which, when the computer program is executed by a computer, cause the computer to carry out: generating a first event label corresponding to a first measurement value of the physiological parameter of the user measured at a first time point; generating a second event label corresponding to a second measurement value of the physiological parameter of the user measured at a second time point; calculating a time difference between the first and second time points; determining whether or not the time difference is smaller than a first time length threshold; upon determining that the time difference is smaller than the first time length threshold, calculating a measurement value difference between the first and second measurement values; and providing an analysis outcome based on the first event label, the second event label, and the measurement value difference.

BRIEF DESCRIPTION OF THE DRAWINGS

Other features and advantages of the disclosure will become apparent in the following detailed description of the embodiment(s) with reference to the accompanying drawings, of which:

FIG. 6 shows a display screen to illustrate an event matching pair and a corresponding reference value;

DETAILED DESCRIPTION

Figure 1:
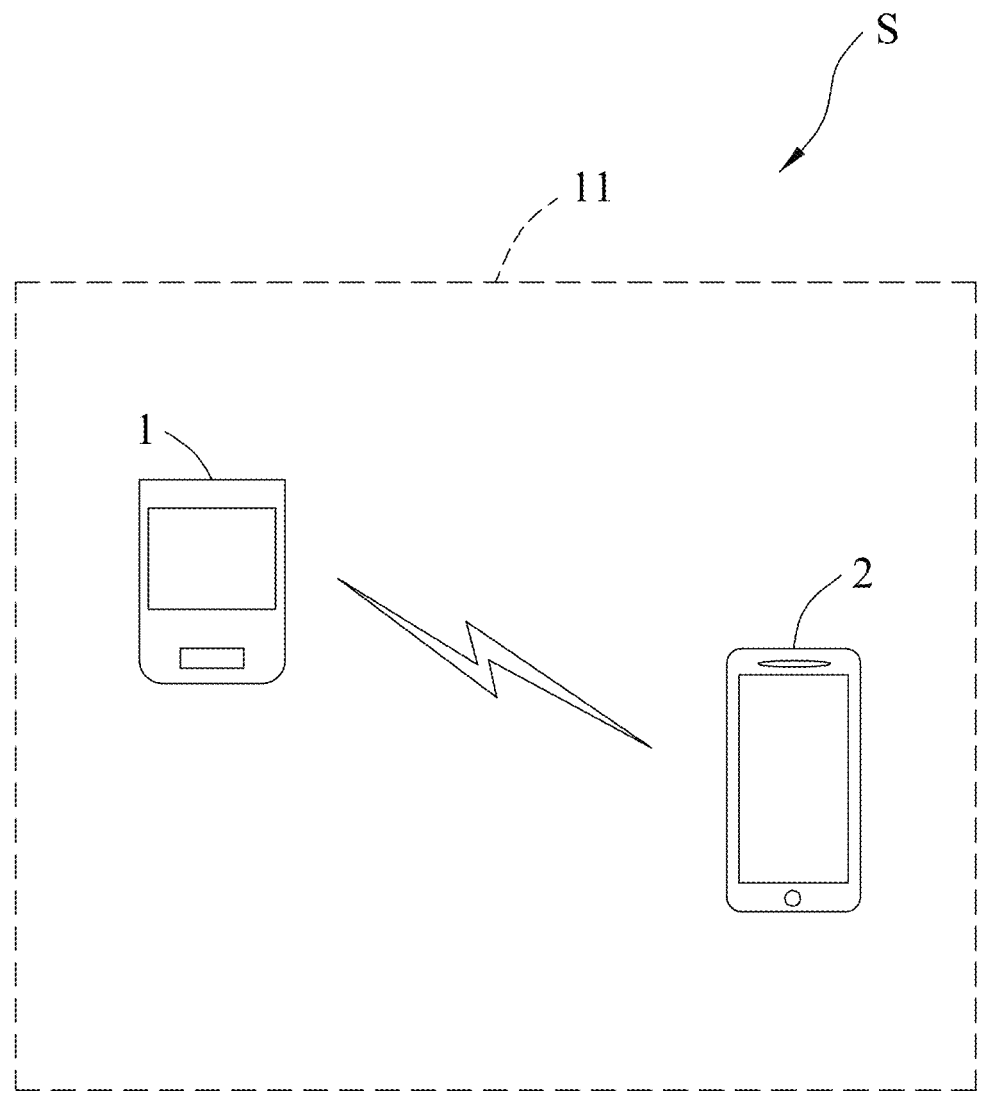
FIG. 1 is a schematic diagram illustrating a computerized physiological parameter measurement system to implement an embodiment of a method for dynamic analysis of a physiological parameter of a user according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, the embodiment of the method for dynamic analysis of a physiological parameter of a user according to this disclosure is shown to be implemented by a computerized physiological parameter measurement system (S) which includes a first physiological parameter measurement apparatus 11. In this embodiment, the physiological parameter is exemplified but not limited to be blood glucose, and the first physiological parameter measurement apparatus 11 is exemplified to include a first blood glucose measuring device 1 adapted for personal use, and a mobile device 2. The mobile device 2 may be a smartphone, a tablet computer, a notebook computer, a wearable device, etc., which is capable of connection to the first blood glucose measuring device 1 via wireless communication technology such as WiFi, Bluetooth, etc., or wired connection. In one implementation, the physiological parameter measurement apparatus 11 is a blood glucose measuring device integrated with functionalities of network communication and computation, and the mobile device 2 is omitted in such implementation. In one embodiment, the physiological parameter measurement apparatus 11 is a mobile device capable of measuring blood glucose, which may be a built-in function or be implemented via external connection to a blood glucose measurement module, so that an independent blood glucose measuring device can be omitted. A software application, which can be built in the physiological parameter measurement apparatus 11 or acquired from external sources such as downloaded from the Internet, may be executed by the physiological parameter measurement apparatus 11 to collect and analyze measured blood glucose data. In this embodiment, the software application is installed in the mobile device 2.

Figure 2:
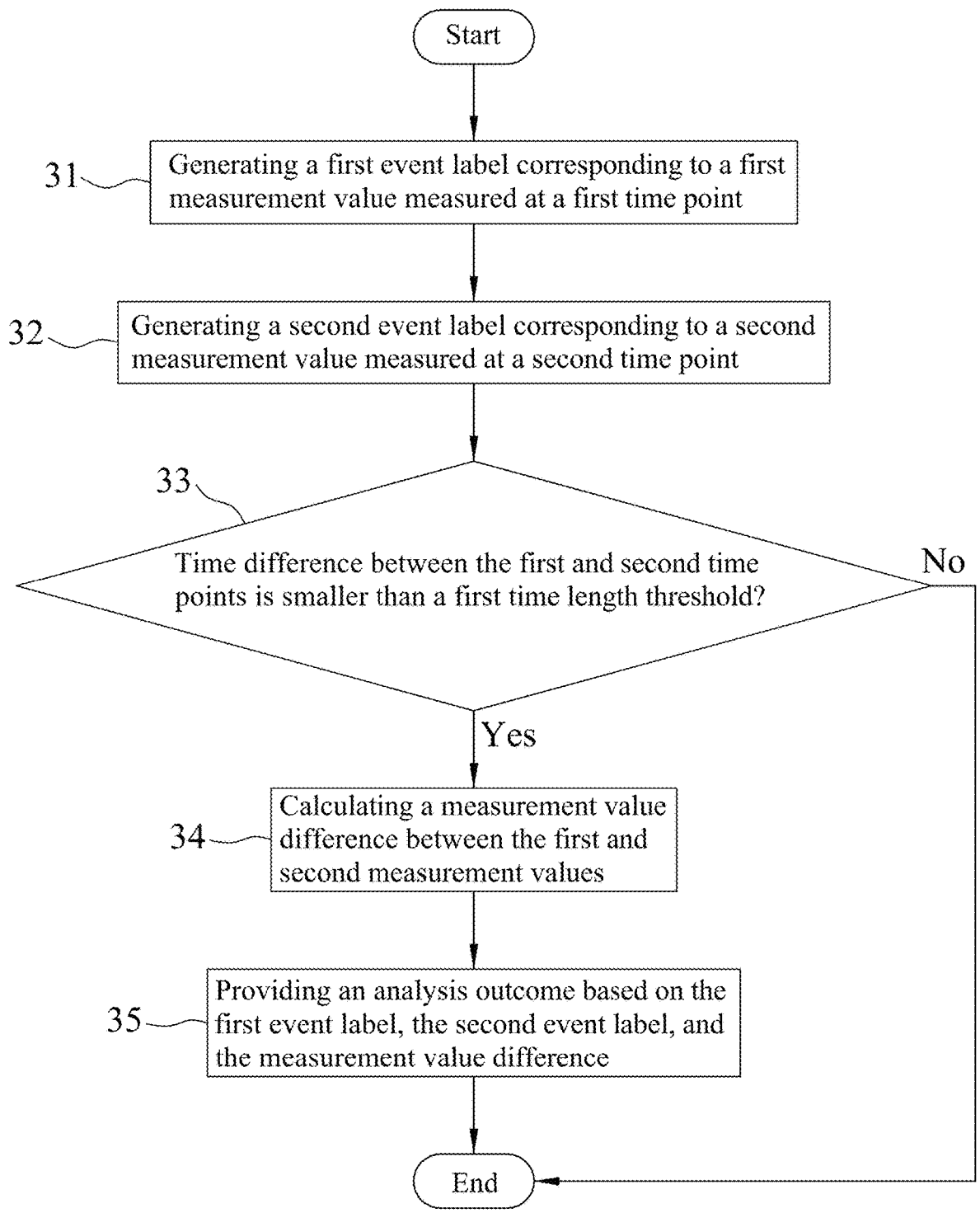
FIG. 2 is a flowchart illustrating steps of the embodiment.

Referring to FIG. 2, in step 31, the user operates the first blood glucose measuring device 1 to perform a measurement of his/her blood glucose level at a first time point to generate data including a first measurement value and a corresponding first event label, and to optionally define the first event label, followed by operating the mobile device 2 to receive, from the first blood glucose measuring device 1, the first measurement value and a data sequence formed by data corresponding to the first measurement value. For instance, to define the first event label, one may operate a user interface of the first blood glucose measuring device 1 to select, from among a plurality of predefined label definitions, e.g., "before meal", "after meal", "before insulin injection", "after insulin injection", etc., one label definition for the first event label. The data sequence corresponding to a measurement value may include information of an event label (e.g., the first event label), a serial number of the corresponding measurement, measurement time at which the measurement value (e.g., the first measurement value) is measured, coordinated universal time (UTC) corresponding to the measurement time, measurement date, a time zone in which the corresponding measurement is performed, a model name of the first blood glucose measuring device 1, a serial number of the first blood glucose measuring device 1, a user account associated with the user, an index indicating whether or not the measurement value is measured from a control solution, an index indicating whether or not temperature at which the measurement is performed is outside of a predetermined criterion, a data type of the measurement value (e.g., indicating that the first measurement value is generated by a blood glucose measuring device or is a manual input), etc. When the first measurement value is transmitted to the mobile device 2, the mobile device 2 may record the longitude and latitude of a current location of the mobile device 2 which may serve as the location at which the corresponding measurement is performed. Table 1 lists the abovementioned parameters and corresponding format:

TABLE 1

| Name | Format |
|---|---|
| Serial No. of Measurement | INTEGER |
| User Account | INTEGER |
| Measurement Time | TEXT |
| Measurement Date | TEXT |
| Measurement Time (UTC) | DATE |
| Time Zone of Measurement | TEXT |
| Measurement Value | INTEGER |
| Event Label | INTEGER |
| Index related to Control Material | INTEGER |
| Index related to Temperature | INTEGER |
| Data Type | INTEGER |
| Device Model | TEXT |
| Device Serial No. | TEXT |
| Longitude of Measurement | REAL |
| Latitude of Measurement | REAL |

In one embodiment, the user directly operates the mobile device 2 to manually input a blood glucose value to serve as the first measurement value, and selectively defines the first event label corresponding to the blood glucose value (first measurement value).

In this embodiment, there are three label types for the event label, the first one of which is a "before event" type, indicating that the blood glucose measurement is performed before occurrence of a specific event, the second one of which is an "after event" type, indicating that the blood glucose measurement is performed after occurrence of a specific event, and the third one of which is a "null" type, indicating lack of correspondence to a specific event. An event label may be automatically determined by the first blood glucose measuring device 1 or the mobile device 2 to correspond to "null" type when the first blood glucose measuring device 1 or the mobile device 2 determines that the user did not define the event label for the corresponding measurement value (e.g., the user did not perform a user input operation on an interface of the first blood glucose measuring device 1 or the mobile device 2 to manually determine a label definition). The specific event may correspond to one of a plurality of predetermined event categories, such as "meal", "exercise", "medication intake", "injection of insulin", etc. As an example, the first label type may indicate a condition of "before meal", "fasting" (a special condition of "before meal"), "before exercise", "before medication", "before injection of insulin", etc., and the second label type may indicate a condition of "after meal", "after exercise", "after medication", "after injection of insulin", etc. In the following description, the first and second label types will be exemplified to mean "before meal" and "after meal" for illustration purposes, but this disclosure is not limited to such implementation.

Figure 3:
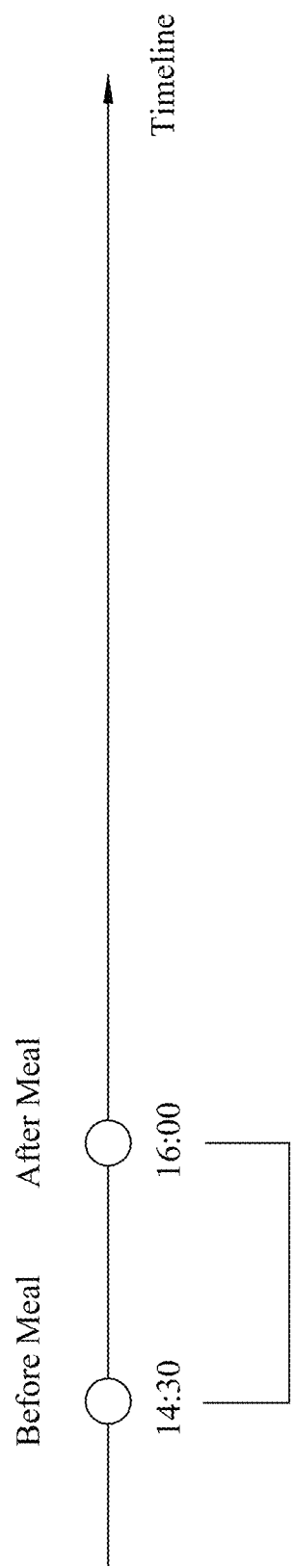
FIG. 3 is a schematic diagram illustrating an event matching pair formed by measurement values labeled by the user.

As exemplified in FIG. 3, the user may operate the first blood glucose measuring device 1 to obtain a first measurement value of blood glucose level at a first time point of "14:30", and to define the corresponding first event label to be "Before Meal", followed by operating the mobile device 2 to receive the first measurement value and the corresponding data sequence from the first blood glucose measuring device 1 (step 31).

In step 32, the user operates the first blood glucose measuring device 1 to measure his/her blood glucose level at a second time point which is later than the first time point to obtain a second measurement value, and to optionally define a corresponding second event label, followed by operating the mobile device 2 to receive, from the first blood glucose measuring device 1, the second measurement value and a data sequence formed by data corresponding to the second measurement value. In one embodiment, the user may directly operate the mobile device 2 to manually input a blood glucose level to serve as the second measurement value, and selectively define the corresponding second event label. In FIG. 3, it is exemplified that the user measured the second measurement value of blood glucose level at "16:00", and define the second event label to be "After Meal".

In step 33, the mobile device 2 calculates a time difference between the first and second time points, and determines whether or not the time difference is smaller than a first time length threshold. When the determination is affirmative, the flow goes to step 34, in which the mobile device 2 calculates a measurement value difference between the first and second measurement values. Then, the mobile device 2 can provide an analysis outcome based on the first event label, the second event label, and the measurement value difference (step 35). Particularly, the measurement value difference is calculated by subtracting the first measurement value from the second measurement value.

Figure 4:
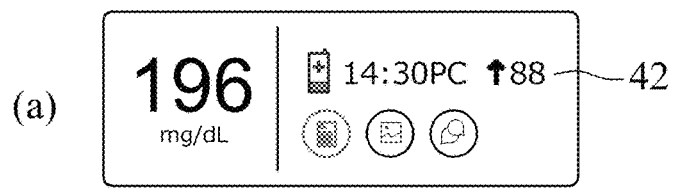
FIG. 4 shows multiple display screens to illustrate multiple implementations of provision of an analysis outcome by way of outputting data according to this disclosure.
Figure 4:
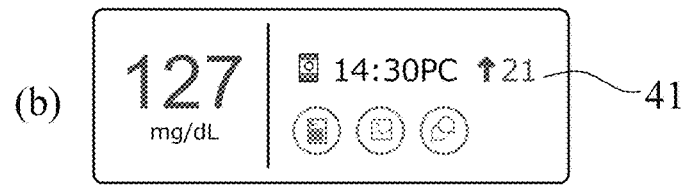
Figure 4:
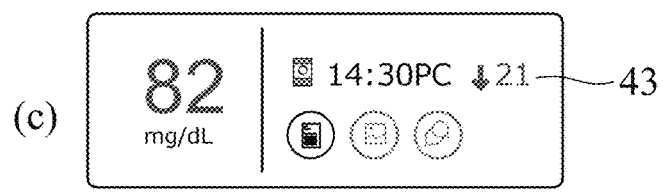

As exemplified in FIG. 3, blood glucose level variation is analyzed based on an event matching pair formed by two measurement values corresponding to the event labels of "Before Meal" and "After Meal". In general, a person may have relatively apparent variation in blood glucose level within four hours post dining, so the first time length threshold may be set at four hours in the software application. In FIG. 3, since the time difference between "16:00" and "14:30" is smaller than four hours (i.e., the first time length threshold), the mobile device 2 calculates the measurement value difference between the first measurement value, which is measured at 14:30, and the second measurement value, which is measured at 16:00. Particularly, in FIG. 4, the software application may further be set with a first glycemic threshold and a second glycemic threshold that is smaller than the first glycemic threshold. Upon determining that the measurement value difference is greater than the first glycemic threshold and the second measurement value is greater than the first measurement value, the mobile device 2 may provide the analysis outcome by outputting a message 42 indicating excessive glycemic increment, as shown in part (a) of FIG. 4; upon determining that the measurement value difference is smaller than the second glycemic threshold and the second measurement value is greater than the first measurement value, the mobile device 2 may provide the analysis outcome by outputting a message 41 indicating insufficient glycemic increment, as shown in part (b) of FIG. 4; and upon determining that the second measurement value is smaller than the first measurement value, the mobile device 2 may provide the analysis outcome by outputting a message 43 indicating after-event glycemic decrement, as shown in part (c) of FIG. 4. In this embodiment, the first glycemic threshold is between 50 mg/dL and 70 mg/dL, such as 60 mg/dL, and the second glycemic threshold is between 20 mg/dL and 40 mg/dL, such as 30 mg/dL. In other words, when the measurement value difference is between 30 mg/dL and 60 mg/dL, the increment degree in blood glucose level would be determined to be normal. In part (d) of FIG. 4, each of the above messages may be represented in a form of an underline 44, 45 of a distinct color that appears below measurement values of a corresponding event matching pair, with the different colors of underline respectively indicating "excessive glycemic increment", "insufficient glycemic increment" and "after-event glycemic decrement", so as to notify a doctor/physician and the user of any abnormal glycemic condition.

Figure 5:
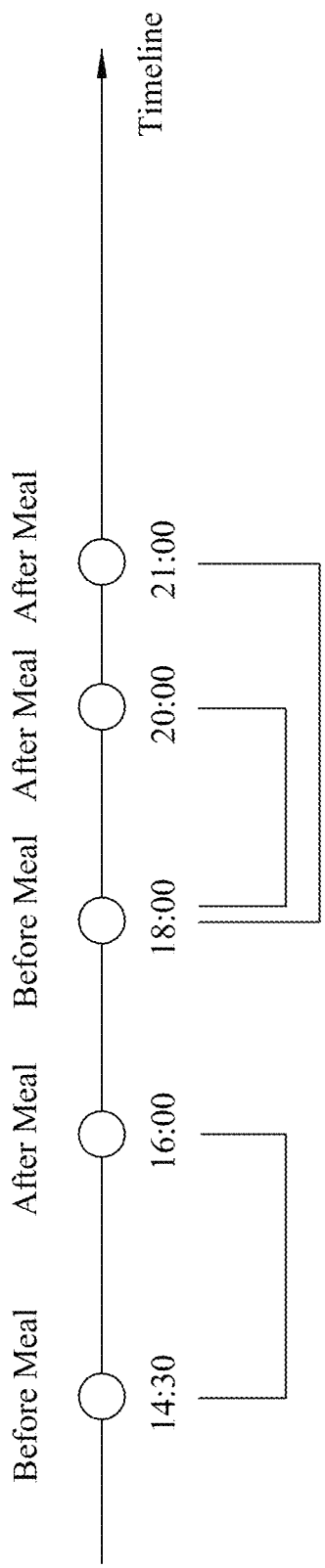
FIG. 5 is a schematic diagram illustrating an example in which a measurement value is paired with two other measurement values based on the time differences and the event labels.

FIG. 5 shows more event matching pairs (i.e., pairs of measurement values acquired before and after respective specific events) corresponding to the event category of "Meal", and indicates that the user further measured his/her blood glucose level at 18:00, 20:00 and 21:00 to generate three more measurement values which are tagged with the event labels of "Before Meal", "After Meal" and "After Meal", respectively. Since a time difference between 18:00 and 20:00 is smaller than four hours (i.e., the first time length threshold), the corresponding measurement values form an event matching pair, and so do the measurement values acquired respectively at 18:00 and 21:00. In practice, when the software application only has the measurement values corresponding to "18:00" and "20:00" while the measurement value taken at 21:00 has not been provided to the software application, there is only one event matching pair formed by the measurement values corresponding to "18:00" and "20:00"; after input of the measurement value corresponding to "21:00" into the software application, since the measurement value corresponding to "21:00" is relatively recent in comparison to the measurement value corresponding to "20:00" and since "21:00" is within four hours from "18:00", variation between the measurement values taken at "18:00" and "21:00" should be greater than that between the measurement values taken at "18:00" and "20:00", so the measurement value corresponding to "21:00" may have greater referential significance than the measurement value corresponding to "20:00" for medical professionals. As a result, the software application may be designed to designate the event matching pair formed by the measurement values corresponding to "18:00" and "21:00" as a primary event matching pair for this event, and to designate the measurement value corresponding to "20:00" as a reference value for this event. In other words, with a newly-inputted measurement value, the software application will search for the measurement values measured within four hours before and after a time point at which the newly-inputted measurement value is measured to match with the newly-inputted measurement value based on the corresponding event labels. Accordingly, when the measurement value corresponding to "21:00" that has the event label of "After Meal" is inputted, the software application will look for a measurement value with an event label of "Before Meal" to perform matching. In this case, the measurement value corresponding to "18:00" is found to perform matching with the measurement value corresponding to "21:00", and the software application designates the measurement value corresponding to "20:00" which is originally paired with the measurement value corresponding to "18:00" as a reference value. As exemplified in FIG. 6 where it is assumed that the measurement values corresponding to "18:00", "20:00" and "21:00" respectively are 90 mg/dL, 132 mg/dL and 151 mg/dL, the measurement value corresponding to "20:00" (i.e., 132 mg/dL) would be displayed under the event matching pair of the measurement values corresponding to "18:00" and "21:00" according to the event label for the measurement value corresponding to "20:00" (i.e., "After Meal"). In addition, the software application may estimate the times of daily routines, such as dining time of the user, based on the measurement time and the event labels, assisting medical professionals and/or the user in illness control.

In practice, the user may omit to define the event label for the measurement value, so that the event label would correspond to the label type of "null". In this embodiment, the software application is configured to automatically alter the label type of an event label which corresponds to the label type of "null" from "null" to either "before event" or "after event", so that the corresponding measurement value can be matched with another measurement value and included in the data used for analysis, enhancing precision/accuracy of analysis.

Figure 7:
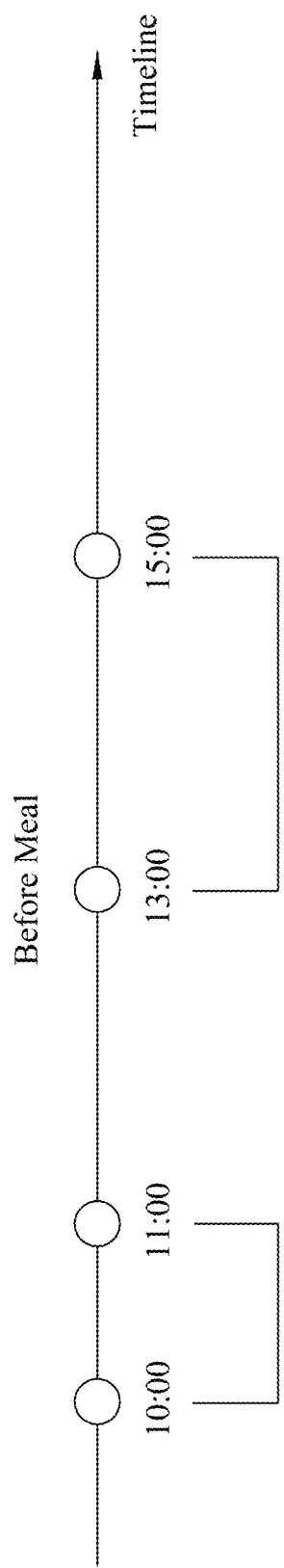
FIG. 7 is a schematic diagram illustrating an example of automatic labeling according to this disclosure.

As exemplified in FIG. 7, the user performed blood glucose measurements to obtain measurement values at 10:00, 11:00, 13:00 and 15:00 on the same day, respectively, wherein only the event label for the measurement value corresponding to "13:00" is manually defined to be "Before Meal", while the other measurement values correspond to the label type of "null" due to the lack of user input for definition. In this case, since the time difference between the earliest time points 10:00 and 11:00 is shorter than four hours, the software application automatically defines the event labels for the measurement values corresponding to "10:00" and "11:00" to be "Before Meal" and "After Meal" respectively, and pairs these two measurement values to form an event matching pair. In addition, since the measurement value corresponding to "13:00" already has the event label of "Before Meal" and the time difference between 13:00 and the following time point 15:00 is shorter than four hours, the software application automatically defines the event label for the measurement value corresponding to "15:00" to be "After meal", and pairs the measurement values corresponding to "13:00" and "15:00" to form an event matching pair. It is noted that the software application is configured to form an event matching pair based on the event labels which respectively indicate that the corresponding measurements were performed before and after the same event, and based on the measurement time corresponding to the measurements. Accordingly, although each of the time difference between 10:00 and 13:00 and the time difference between 11:00 and 13:00 is shorter than four hours, the corresponding measurement values will not be paired up to form an event matching pair.

Figure 8:
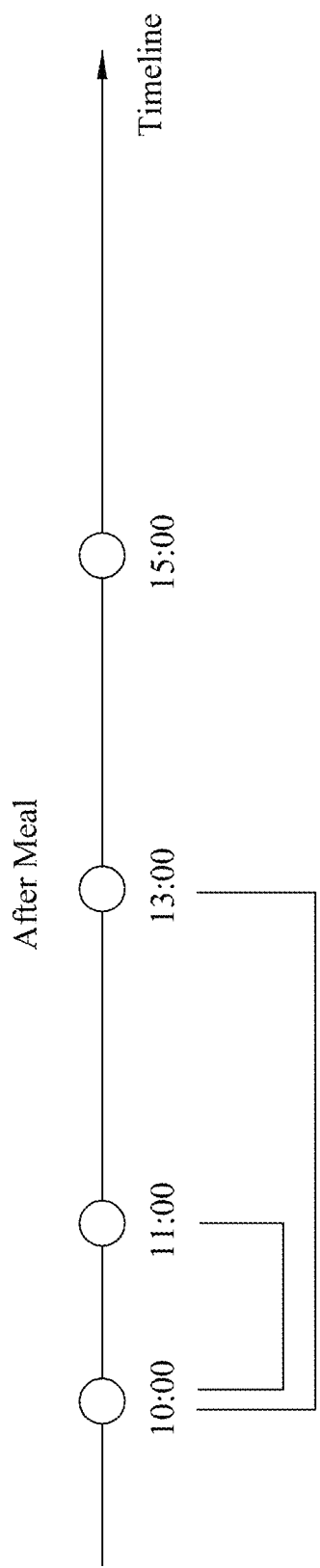
FIG. 8 is a schematic diagram illustrating another example of automatic labeling according to this disclosure.

In FIG. 8, it is exemplified that the user only defines the event label for the measurement value taken at "13:00" to be "After Meal". In this case, since the time difference between the earliest two time points 10:00 and 11:00 is shorter than four hours, the software application automatically pairs the measurement values corresponding thereto to form an event matching pair, and defines the event labels for these two measurement values to be "Before Meal" and "After Meal", respectively. When the measurement value corresponding to "13:00", for which the event label is defined to be "After Meal", is inputted as a third measurement value, the software application searches for any measurement value measured within four hours before or after 13:00 for pairing based on the event label "After Meal", and forms an event matching pair using the measurement values taken at "10:00" and "13:00" since the event label for the measurement value corresponding to "10:00" is "Before Meal", and designates the measurement value taken at "11:00" as a reference value for the "Meal" event. Further, the measurement value corresponding to "15:00" will be labeled as a measurement value of the next event, and possibly form an event matching pair with a subsequent measurement value measured less than 4 hours apart. In this case, although the event label for the measurement value corresponding to "11:00" is automatically defined by the software application to be "After Meal", and the measurement values corresponding to "10:00" and "11:00" are paired up to form an event matching pair, the later inputted measurement value at 13:00 causes the measurement value corresponding to "11:00" to become a reference value for the same event, while the measurement value corresponding to "10:00" is switched to be paired up with the measurement value corresponding to "13:00". That is, conditions of the event matching pairs may change dynamically based on newly inputted measurement values.

Figure 9:
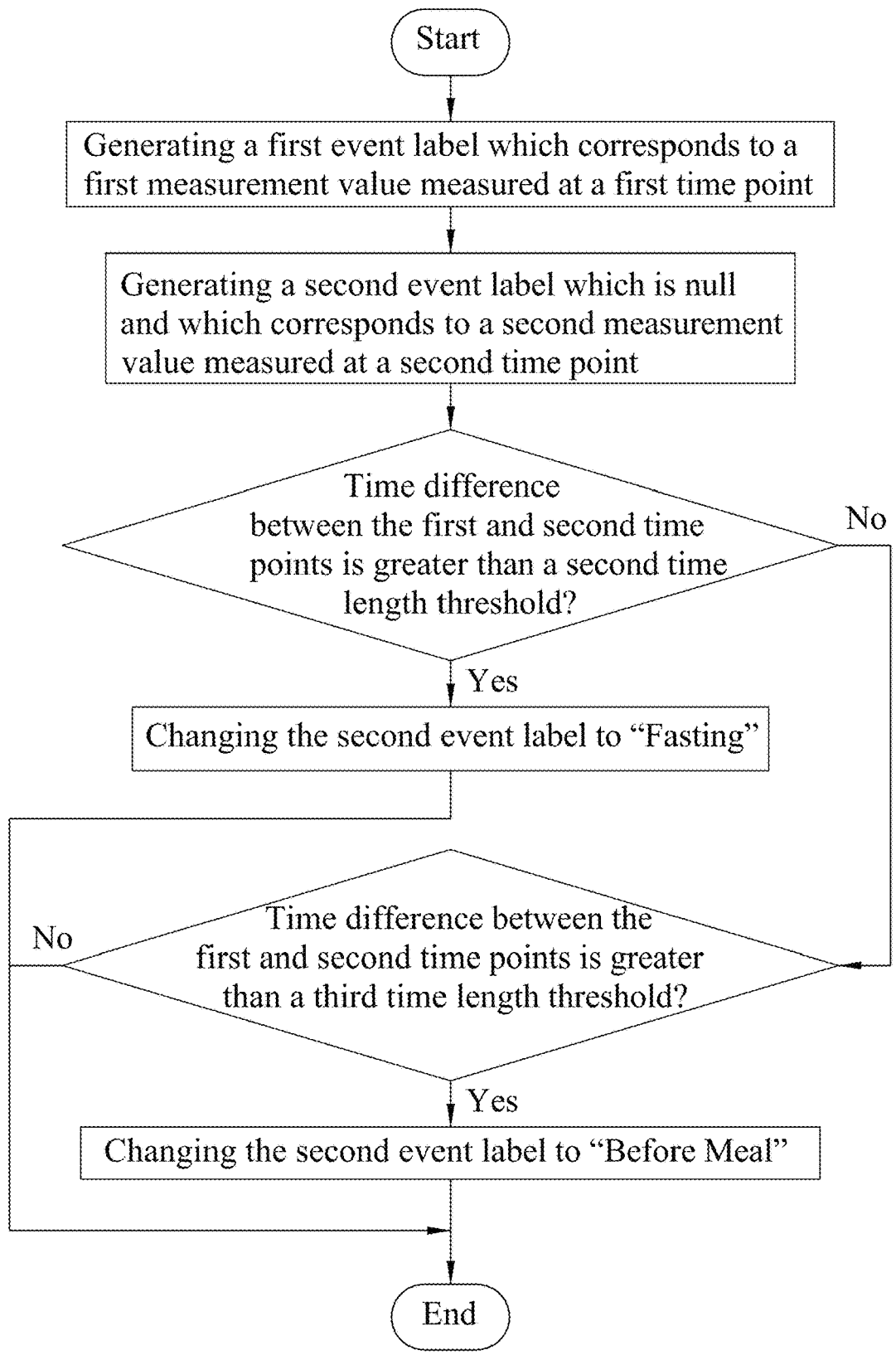
FIG. 9 is a flowchart illustrating steps of automatic labeling of event labels of "Fasting" and "Before Meal" according to this disclosure.

Referring to FIG. 9, when the measurement for the second measurement value is next to the measurement for the first measurement value in terms of time (i.e., no measurement is performed between the first and second time points), the software application further determines whether or not the time difference between the first and second time points is greater than a second time length threshold which is greater than the first time length threshold when the second event label corresponds to the label type of "null". Upon determining that the time difference is greater than the second time length threshold, the software application changes the second event label to "Fasting", which represents a special condition of "Before Meal". In general, a blood glucose level measured under a condition that the user has not consumed food for over eight hours is considered fasting plasma glucose, so the second time length threshold may be set at eight hours. In addition, the software application may be further configured to determine whether or not the time difference between the first and second time points is greater than a third time length threshold which is not smaller than the first time length threshold but is smaller than the second time length threshold. Upon determining that the time difference is between the second time length threshold and the third time length threshold, the software application may change the second event label to "Before Meal". In general, a blood glucose level measured under a condition that the user has not consumed food for over five hours but less than eight hours is considered preprandial plasma glucose, so the third time length threshold may be set at five hours.

Figure 10:
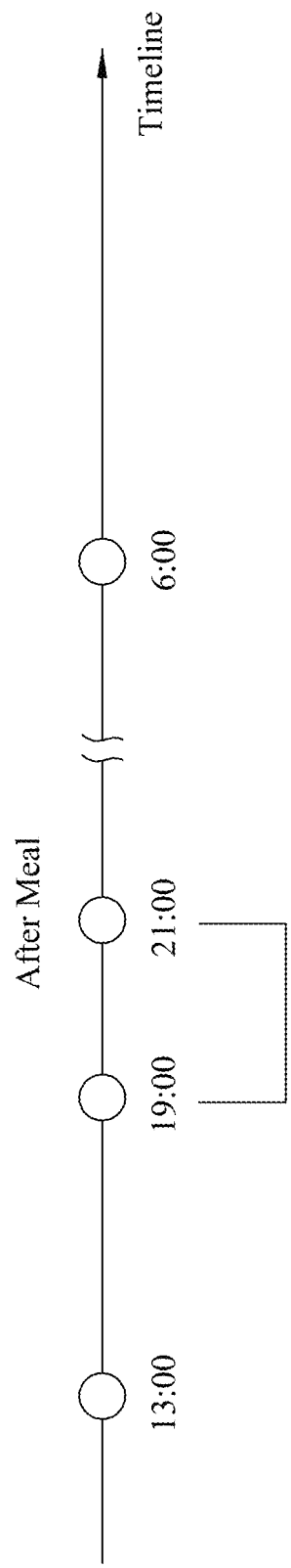
FIG. 10 is a schematic diagram illustrating an example of automatic labeling according to the flow in FIG. 9.

As exemplified in FIG. 10, although the event label for the measurement value taken at time point "6:00" is not defined manually, it would be automatically defined to be "Fasting" by the software application since a time difference between this measurement value and an immediately previous one, which was taken at 21:00 a day before, is longer than eight hours. In FIG. 10, the event label for the measurement value corresponding to "19:00" is not defined by the user either, and it would be automatically defined to be "Before Meal" since the time difference from the last measurement (i.e., taken at "13:00") is longer than five hours but shorter than eight hours.

Accordingly, the software application may be configured to, for a measurement value for which the event label is not manually defined, automatically define the event label for the same based on the corresponding measurement time and a relationship thereof with the previous measurement value (or even later change the event label based on a next measurement value), and optionally cause the measurement value to form an event matching pair with another measurement value.

In addition to providing notification messages for indicating "excessive glycemic increment", "insufficient glycemic increment" and "after-event glycemic decrement", the software application may further store measurement information, such as the measurement values, the associated event labels, the time differences among the measurement values, the measurement value differences, etc., in the mobile device 2, so that the user may track his/her blood glucose level variation before and after a meal or other events, and provide the measurement information to medical professionals as a reference in making a diagnosis.

As a result, in this embodiment, it is not necessary for the user to preset the dining time for the mobile device 2 to determine whether a measurement is performed before or after a meal, and the user can selectively define the event labels for all or some measurement values that are acquired before or after an arbitrary dining time, so that the mobile device 2 that executes the software application may automatically define the event label(s) for the remaining measurement value(s), if any, based on the user-input event label(s), and analyze whether the blood glucose level variation(s) of the event matching pair(s) is within a predetermined criterion or not. With the accumulation of the blood glucose measurement information, the software application may analyze the daily routines of the user, such as dining time and bedtime.

Figure 11:
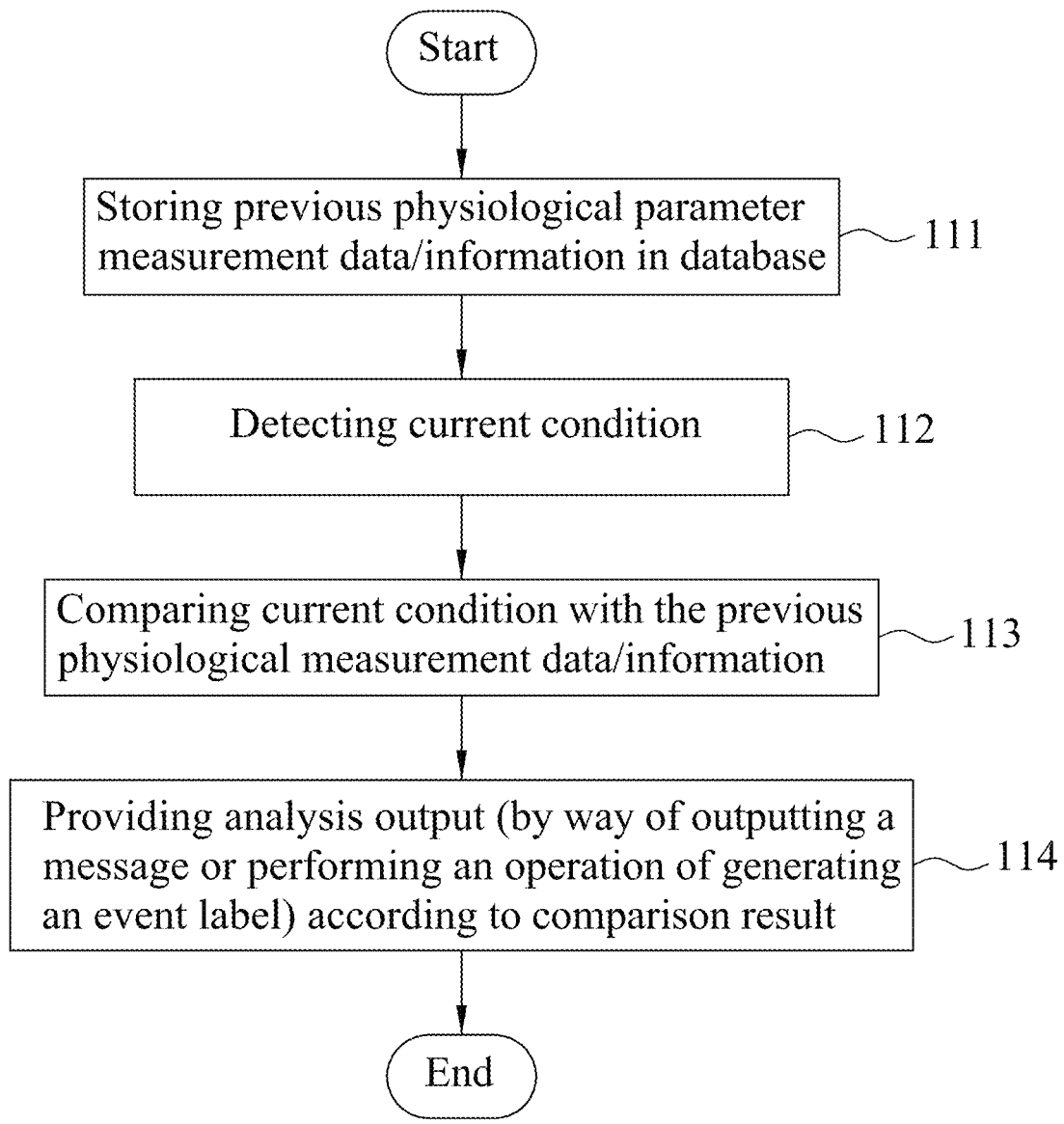
FIG. 11 is a flowchart illustrating steps of providing an analysis outcome based on comparison between a current time point and previous physiological parameter measurement data.

Referring to FIG. 11, the software application may store, in a database of the mobile device 2, previous physiological parameter measurement data (step 111) including the measurement information regarding multiple blood glucose measurements that are previously performed in correspondence to multiple events, and time information regarding multiple event time segments respectively corresponding to the events. The mobile device 2 that executes the software application may detect a current condition (e.g., current time, date, location, etc.) related to the mobile device 2 (step 112) and then compare the current condition (e.g., a current time point) with the event time segments to generate a comparison result based on the comparison (step 113). In step 114, the mobile device 2 may provide the analysis outcome by providing the comparison result. For example, the comparison result may be a notification message or a warning message for reminding the user to take a blood glucose measurement or take medication, and the mobile device 2 may provide the comparison result by outputting the notification or warning message in the form of, e.g., a visual message, sound or a combination thereof. Alternatively, the mobile device 2 may provide the comparison result by performing an operation to define the event labels for the measurement values. This disclosure is not limited in this respect.

For instance, when the user used to have a "Before Meal" measurement value of blood glucose level at around 9:00 and an "After Meal" measurement value of blood glucose level at around 10:00 on Saturdays, according to the measurement information stored in the database, the software application may determine that the user routinely has breakfast between 9:00 and 10:00 on Saturdays, and thus automatically provide a notification message between 9:00 and 10:00 on Saturdays to remind the user to perform blood glucose measurements before and after having breakfast. Furthermore, the software application may automatically and appropriately define the event labels for the measurement values based on the analyzed time segments for performing the daily routines which are not defined with event labels by the user. As an example, when the software application determines that time segments for breakfast are mostly between 9:00 and 10:00, the event label which corresponds to a measurement value measured between 8:00 and 10:00 and which is not defined by the user may be automatically defined to be "Before Meal", and the event label which corresponds to a measurement value measured within, for example, four hours after the determined breakfast time segment (i.e., between 10:00 and 14:00 for the determined breakfast time segment being between 9:00 and 10:00 in this example), and which is not defined by the user may be automatically defined to be "After Meal".

In one embodiment, the software application may further provide warning/advisory messages based on previous blood glucose level variations that are recorded in the database. For example, when the analysis result shows that the user frequently has excessive glycemic increment after dinner (corresponding to the time segment between 18:00 and 20:00) on Fridays, the software application may provide a warning message for reminding food control, and an advisory message for advising appropriate dining. By the software application learning the daily routines of the user via data analysis, illness control may be enhanced, and the user may be motivated to continue with the measurements, so the measurement records may be more complete and more valuable to medical professionals in providing medical advice.

Figure 12:
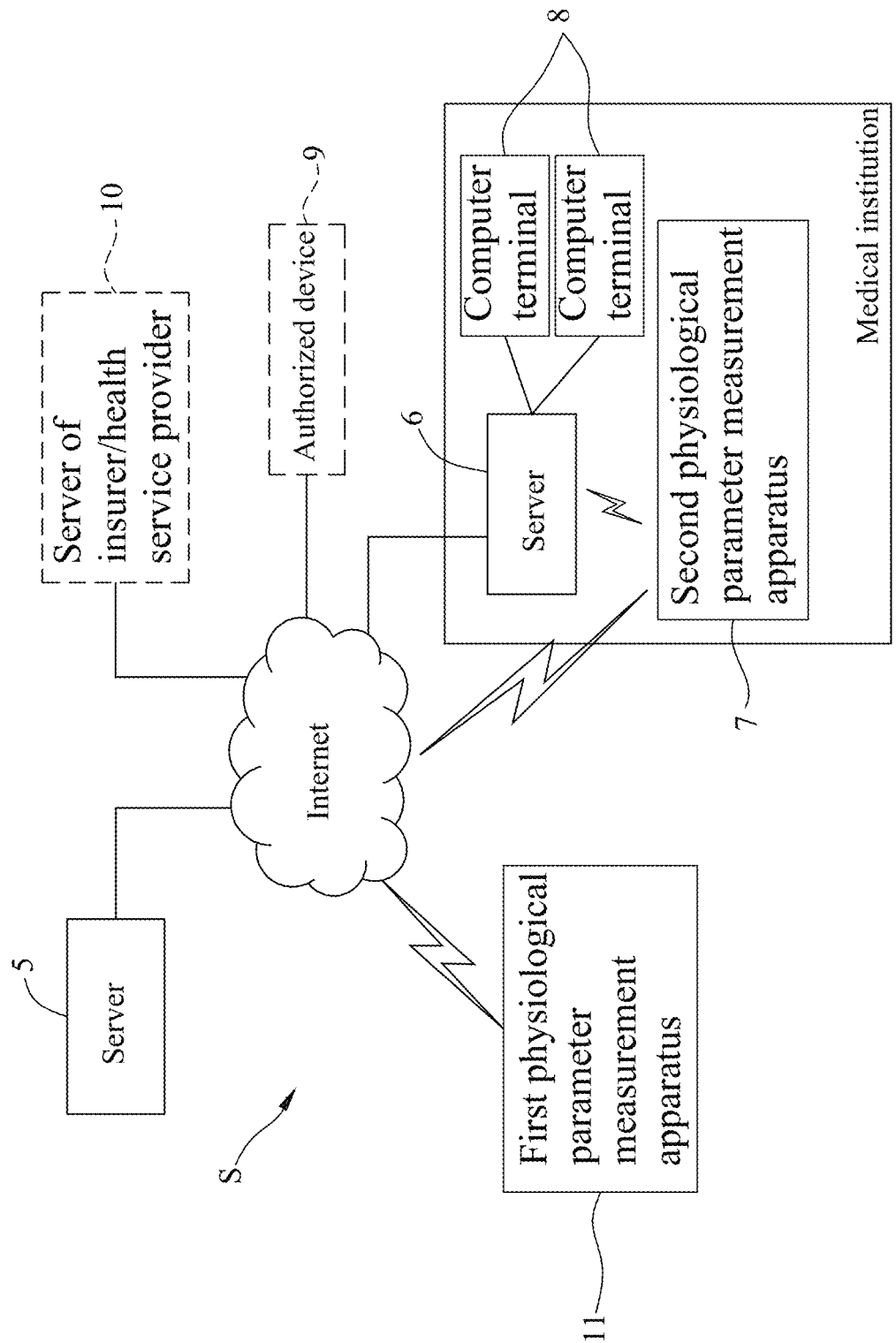
FIG. 12 is a block diagram showing another implementation of the computerized physiological parameter measurement system.

Referring to FIG. 12, in one embodiment, the computerized physiological parameter measurement system (S) further includes a server 5, and a second physiological parameter measurement apparatus 7 capable of external data transmission. The second physiological parameter measurement apparatus 7 is a professional instrument designed for use by medical professionals and placed in a medical institution, and is connected to a server 6 of the medical institution via a wired or wireless network. The medical institution may have multiple computer terminals 8, each of which may be a desktop computer, a notebook computer, a tablet computer, a smartphone, etc., and which are connected to the server 6. When the user's blood glucose level is measured in the medical institution using the second physiological parameter measurement apparatus 7, the measurement value may be uploaded to the server 6 by the second physiological parameter measurement apparatus 7 and transmitted to the server 5 via the server 6 which is connected to the Internet, and the mobile device 2 (see FIG. 1) may receive the measurement value from the server 5. In one implementation, the second physiological parameter measurement apparatus 7 may be directly coupled to the server 5 via a network, and the measurement value measured by the second physiological parameter measurement apparatus 7 in the medical institution may be directly uploaded to the server 5 without passing through the server 6. Similarly, the measurement values measured by the user using the first physiological parameter measurement apparatus 11 can be transmitted to the server 5 through a network, so that the computer terminals 8 and/or the second physiological parameter measurement apparatus 7 can acquire or access these measurement values from the server 5 directly or via the server 6. In one implementation, the server 5 may provide a cloud software application to share a part of the computations otherwise performed by the mobile device 2, and to provide analysis services after input of the measurement data from the first and second physiological parameter measurement apparatuses 11, 7. In one implementation, the server 5 may provide an interface for the mobile device 2, the second physiological parameter measurement apparatus 7, the computer terminals 8, servers 10 of insurers and/or other health server providers, or any other authorized devices 9 to access the measurement data stored therein and analysis results made thereby.

As a result, the mobile device 2, the second physiological parameter measurement apparatus 7, the computer terminals 8, the servers 10 of insurers and/or other health server providers, and the authorized devices 9 may combine the measurement values measured by each of the first and second physiological parameter measurement apparatuses 11, 7 to serve as basis for performing an analysis. In other words, each of the abovementioned first and second measurement values may be acquired using either the first physiological parameter measurement apparatus 11 or the second physiological parameter measurement apparatus 7, and the system (S) (referring to the abovementioned devices that collect the measurement data herein) may distinguish whether each of the measurement values is manually inputted or is measured by which measurement instrument based on the information included in the corresponding data sequence, such as the data type, the apparatus model name, the apparatus serial number, etc. In addition, the system (S) may use personal data of the user to serve as the user account in order to determine each collected measurement value corresponds to which user. The personal data may be a name, a phone number, a date of birth, an identification number, an e-mail address, fingerprint information, voiceprint information, iris information, or combinations thereof, which is presented as a code, such as a one-dimensional code (e.g., the barcode) or a two-dimensional code (e.g., QR code). The medical professionals may scan the code to open the user account using the second physiological parameter measurement apparatus 7 and measure the blood glucose level of the user, thus establishing the correspondence between the measurement value and the user account, and allowing the user account information to be included in the data sequence that corresponds to the measurement value. After the measurement values measured by the first and second physiological parameter measurement apparatuses 11, 7 are transmitted to and stored in the server 5, the server 5 may use the cloud software application to perform analysis according to the embodiment of this disclosure, so that a backup of the analysis result may be recorded in the server 5 or server 6. Accordingly, the user may use the mobile device 2 to make a query of the blood glucose measurement records and the corresponding analysis result with the server 5, and medical professionals may use the computer terminals 8 or the second physiological parameter measurement apparatus 7 to make a query of the blood glucose measurement records and the corresponding analysis result with the server 5 or server 6.

It is noted that the embodiment according to this disclosure is not limited to application associated with the blood glucose levels, and can also be applied to other physiological parameters, such as heart rates, pulse rates, body fat percentage, calorie consumption rates before and after exercise, with use of appropriate measurement apparatus(es)/module (s).

In summary, the method for dynamic analysis of a physiological parameter according to this disclosure can automatically create event matching pairs of measurement values according to the measurement time and the event labels, and further determine, for each event matching pair, whether or not the variation of the physiological parameter before and after the corresponding event is normal. In addition, with the accumulation of the physiological parameter measurement data, the daily routines of the user may be predicted more accurately based on the accumulated measurement data, and the system (S) can thus provide more appropriate medical advice/notification.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for accurate dynamic tracking of a physiological parameter of a user, implemented by a computerized physiological parameter measurement system, the method comprising:

generating a first event label corresponding to a first measurement value of the physiological parameter of the user measured at a first time point, the first event label having one of a first label type, a second label type and a third label type, the first and second label types being defined relative to a specific event;

generating a second event label corresponding to a second measurement value of the physiological parameter of the user measured at a second time point, the second event label having one of the first label type, the second label type and the third label type;

calculating a first time difference between the first and second time points;

comparing the first time difference to a first time length threshold;

determining the first event label to have the first label type and the second event label to have the second label type;

selectively pairing the first and second measurement values to generate an event matching pair corresponding to the specific event based on the comparison of the first time difference with the first time length threshold, the event matching pair having two event-related measurement values respectively set to the first and second measurement values;

generating a third event label that corresponds to a third measurement value of the physiological parameter of the user measured at a third time point;

determining the third event label to have one of the first label type and the second label type;

calculating a second time difference between the third time point and the first time point for a third event label of second label type, comparing the second time difference to the first time length threshold and the first time difference, and selectively pairing the first and third measurement values to update the event matching pair corresponding to the specific event based on the comparison of the second time difference to the first time length threshold and the first time difference, the event matching pair respectively updating the two event-related measurement values to the first and third measurement values;

calculating a third time difference between the third time point and the second time point for a third event label of first label type, comparing the third time difference to the first time length threshold and the first time difference, and selectively pairing the third and second measurement values to update the event matching pair corresponding to the specific event based on the comparison of the third time difference to the first time length threshold and the first time difference, the event matching pair respectively updating the two event-related measurement values to the third and second measurement values; and calculating for the event matching pair a measurement value difference between the two event-related measurement values of the event matching pair, and providing an analysis outcome based on the event matching pair and the measurement value difference, the analysis outcome including an alert warning the user of an abnormal medical condition based on the measurement value difference, the abnormal medical condition being correlated to abnormal variation in the physiological parameter.

2. The method of claim 1, wherein the first time length threshold is four hours.

3. The method of claim 2, wherein the physiological parameter is blood glucose level, the first label type indicates that measurement is performed before occurrence of the specific event, the second label type indicates that measurement is performed after occurrence of the specific event, and a third label type indicates that measurement lacks correspondence to the specific event.

4. The method of claim 3, wherein the specific event corresponds to one of a category of meal, a category of exercise, a category of medication intake, and a category of injection of insulin.

5. The method of claim 3, wherein the first event label is generated having the third label type based on lack of a user type input operation;

wherein the second event label is generated having the third label type based on lack of the user type input operation;

wherein the second time point is later than the first time point; and wherein said method further comprises:

determining each of the first and second event labels to have the third label type, and selectively changing the first event label to have the first label type and changing the second event label to have the second label type based on a comparison of the first time difference to the first time length threshold.

6. The method of claim 3, wherein the first event label is generated having the first label type based on a user type input operation;

wherein the second event label is generated having the third label type based on lack of the user type input operation;

wherein the second time point is later than the first time point; and wherein said method further comprises:

determining the first event label to have the first label type and the second event label to have the third label type, and selectively changing the second event label to have the second label type based on a comparison of the first time difference to the first time length threshold.

7. The method of claim 3, wherein the first event label is generated having the third label type based on lack of a user type input operation;

wherein the second event label is generated having the second label type based on the user type input operation;

wherein the second time point is later than the first time point; and wherein said method further comprises:

determining the first event label to have the third label type and the second event label to have the second label type, and selectively changing the first event label to have the first label type based on a comparison of the first time difference to the first time length threshold.

8. The method of claim 3, wherein the first event label is generated to have the first label type, and the second label is generated to have the second label type; and wherein the analysis outcome includes the first label, the second event label, the measurement value difference, and the event matching pair formed by the first and second measurement values.

9. The method of claim 8, wherein the analysis outcome further includes an indicator of a time segment of the specific event.

10. The method of claim 9, the computerized physiological parameter measurement system storing measurement information regarding multiple physiological parameter measurements that are previously performed in correspondence to multiple events, and time information regarding multiple event time segments respectively corresponding to the events;

said method further comprising: comparing a current time point with the event time segments to generate a comparison result;

wherein the analysis outcome further includes the comparison result.

11. The method of claim 10, wherein providing the comparison result includes at least one of: outputting a notification message, outputting a warning message, or performing an operation to define at least one of the first and second event labels.

12. A system for accurate dynamic tracking of a physiological parameter of a user, comprising:

a measurement part configured to measure the physiological parameter of the user for generating a first event label corresponding to a first measurement value of the physiological parameter of the user measured at a first time point and a second event label corresponding to a second measurement value of the physiological parameter of the user measured at a second time point, the first event label having one of a first label type, a second label type and a third label type, the second event label having one of the first label type, the second label type and the third label type, the first and second label types being defined relative to a specific event; and a computation part communicatively coupled to said measurement part for receiving therefrom measured physiological parameter data including the first event label, the first measurement value, the first time point, the second event label, the second measurement value and the second time point, and configured to:

calculate a first time difference between the first and second time points;

determine whether or not the time difference is smaller than a first time length threshold;

wherein upon determining the first event label to have the first label type and the second event label to have the second label type:

upon determining the first time difference to be smaller than the first time length threshold, pair the first and second measurement values to generate an event matching pair corresponding to the specific event, the event matching pair having two event-related measurement values respectively set to the first and second measurement values;

wherein upon generating a third event label that corresponds to a third measurement value of the physiological parameter of the user measured at a third time point, and upon determining the first event label to have the first label type and the second event label to have the second label type:

upon determining the third event label to have the second label type, calculate a second time difference between the third time point and the first time point, upon determining the second time difference to be smaller than the first time length threshold and greater than the first time difference, pair the first and third measurement values to update the event matching pair corresponding to the specific event, the event matching pair respectively updating the two event-related measurement values to the first and third measurement values, upon determining the third event label to have the first label type, calculate a third time difference between the third time point and the second time point, and upon determining the third time difference to be smaller than the first time length threshold and greater than the first time difference, pair the third and second measurement values to update the event matching pair corresponding to the specific event, the event matching pair respectively updating the two event-related measurement values to the third and second measurement values; and wherein upon generating or updating the event matching pair:

calculate a measurement value difference between the two event-related measurement values of the event matching pair, and provide an analysis outcome based on the event matching pair and the measurement value difference, the analysis outcome including an alert warning the user of an abnormal medical condition based on the measurement value difference, the abnormal medical condition being correlated to abnormal variation in the physiological parameter.

13. The system of claim 12, wherein said measurement part includes a first physiological parameter measurement apparatus for measurement of the physiological parameter of the user, and a second physiological parameter measurement apparatus placed in a medical institution for use by a medical professional to measure the physiological parameter of the user;

said system further comprising a server communicatively coupled to said first and second physiological parameter measurement apparatuses via a network for receiving measured physiological parameter data therefrom;

wherein said first physiological parameter measurement apparatus is further configured to receive physiological parameter data measured by said second physiological parameter measurement apparatus from said server via the network, and said second physiological parameter measurement apparatus is further configured to receive physiological parameter data measured by said first physiological parameter measurement apparatus from said server via the network.

14. A computer program for accurate dynamic tracking of a physiological parameter of a user, comprising instructions encoded on a non-transitory computer readable medium which, when said computer program is executed by a computer, cause the computer to carry out a method including:

generating a first event label corresponding to a first measurement value of the physiological parameter of the user measured at a first time point, the first event label having one of a first label type, a second label type and a third label type, the first and second label types being defined relative to a specific event;

generating a second event label corresponding to a second measurement value of the physiological parameter of the user measured at a second time point, the second event label having one of the first label type, the second label type and the third label type;

calculating a first time difference between the first and second time points;

upon determining the first event label to have the first label type and the second event label to have the second label type, and the first time difference to be smaller than the first time length threshold, pairing the first and second measurement values to generate an event matching pair corresponding to the specific event, the event matching pair having two event-related measurement values respectively set to the first and second measurement values;

generating a third event label that corresponds to a third measurement value of the physiological parameter of the user measured at a third time point;

upon determining the first event label to have the first label type and the second event label to have the second label type:

upon determining the third event label to have the second label type, calculating a second time difference between the third time point and the first time point, upon determining the second time difference to be smaller than the first time length threshold and greater than the first time difference, pairing the first and third measurement values to update the event matching pair corresponding to the specific event, the event matching pair respectively updating the two event-related measurement values to the first and third measurement values, upon determining the third event label to have the first label type, calculating a third time difference between the third time point and the second time point, and upon determining the third time difference to be smaller than the first time length threshold and greater than the first time difference, pairing the third and second measurement values to update the event matching pair corresponding to the specific event, the event matching pair respectively updating the two event-related measurement values to the third and second measurement values; and upon generating or updating the event matching pair:

calculating a measurement value difference between the two event-related measurement values of the event matching pair, and providing an analysis outcome based on the event matching pair and the measurement value difference, the analysis outcome including an alert warning the user of an abnormal medical condition based on the measurement value difference, the abnormal medical condition being correlated to abnormal variation in the physiological parameter.

15. The computer program of claim 14, wherein the measurement for the second measurement value is performed after the measurement for the first measurement value, the measurements for the first and second measurement values are consecutive measurements, and a second time length threshold is greater than the first time length threshold, the method further including:
  upon determining the second event label to have the third label type, determining whether or not the first time difference is greater than the second time length threshold; and
  upon determining the first time difference to be greater than the second time length threshold, changing the second event label to represent a fasting condition and to have the first label type.

16. The computer program of claim 15, wherein a third time length threshold is not smaller than the first time length threshold but is smaller than the second time length threshold, the method further including:
  upon determining the second event label to have the third label type, determining whether or not the first time difference is between the second time length threshold and the third time length threshold; and
  upon determining the first time difference to be between the second time length threshold and the third time length threshold, changing the second event label to represent a preprandial condition and to have the first label type.

17. The computer program of claim 14,
wherein the second time point is later than the first time point, the first label is generated to have the first label type indicating that measurement is performed before occurrence of a specific event, and the second label is generated to have the second label type indicating that measurement is performed after occurrence of the specific event.

18. The computer program of claim 14,
wherein the second time point is later than the first time point, and the physiological parameter is blood glucose level;
wherein the alert of the analysis outcome includes a message indicating excessive glycemic increment when the second measurement value is greater than the first measurement value, and the measurement value difference between the first and second measurement values is greater than a first glycemic threshold;
wherein the alert of the analysis outcome includes a message indicating insufficient glycemic increment when the second measurement value is greater than the first measurement value, and the measurement value difference between the first and second measurement values is smaller than a second glycemic threshold which is smaller than the first glycemic threshold; and
wherein the alert of the analysis outcome includes a message indicating after-event glycemic decrement when the second measurement value is smaller than the first measurement value.

19. The computer program of claim 14,
wherein the second time point is later than the first time point, the second time difference is smaller than the first time length threshold and greater than the first time difference, the first event label is generated to have the first label type indicating that measurement is performed before occurrence of a specific event, and the second event label is generated to have the second label type indicating that measurement is performed after occurrence of the specific event; and
wherein, when updating the event matching pair upon generating the third event label, upon determining the third event label to have the second label type, the second measurement value is set to be a reference value associated with the event matching pair.

* * * * *